United States Patent [19]

Tsujimoto et al.

[11] 4,058,017
[45] Nov. 15, 1977

[54] AUTOMATIC PROBE FEEDING, SETTING AND WITHDRAWING APPARATUS

[75] Inventors: Kenichi Tsujimoto; Yoshiharu Ikeuchi; Akira Kuriyama, all of Wakayama, Japan

[73] Assignee: Sumitomo Metal Industries Ltd., Osaka, Japan

[21] Appl. No.: 703,426

[22] Filed: July 8, 1976

[30] Foreign Application Priority Data

| July 11, 1975 | Japan | 50-85601 |
|---|---|---|
| July 19, 1975 | Japan | 50-88954 |
| July 15, 1975 | Japan | 50-98664[U] |
| July 15, 1975 | Japan | 50-98665[U] |

[51] Int. Cl.$^2$ ............................................. G01N 1/04
[52] U.S. Cl. .................................. 73/423 R; 83/490; 221/298
[58] Field of Search .................. 73/423 R, 423 A; 83/490; 221/298, 290

[56] References Cited

U.S. PATENT DOCUMENTS

| 3,189,217 | 6/1965 | Clase | 221/298 X |
| 3,211,005 | 10/1965 | Baudier | 73/423 R X |
| 3,487,696 | 1/1970 | Hoffa | 73/423 A |
| 3,515,190 | 6/1970 | Morinchi | 83/490 X |
| 3,837,528 | 9/1974 | Rakucewicz | 221/298 X |

*Primary Examiner*—Richard C. Queisser
*Assistant Examiner*—Charles Gorenstein
*Attorney, Agent, or Firm*—Watson, Cole, Grindle & Watson

[57] ABSTRACT

An automatic probe feeding, setting and withdrawing apparatus includes a probe container case provided with a probe dispensing mechanism for dispensing individual probes to a probe transfer mechanism. The probe transfer mechanism has a motor-driven probe push member provided at one end of a carriage board formed with a V-shaped channel in its surface. The probes are transferred to a probe setting mechanism which has a movable block capable of making sliding movement through a given stroke by the operation a cylinder on a support board mounted for pivotal movement by the operation of a cylinder. The probes are moved from a horizontal to a vertical orientation by this probe-setting mechanism. The probes are so positioned that they can be grasped by a probe holding rod and can be appropriately inserted into a furnace for measurement of conditions therein. Thereafter, with the probes removed from the furnace, they are transferred to a probe withdrawing and recovering mechanism. The mechanism comprises a probe grasping mechanism having a pair of probe grasping pawls pivotally secured to two interengaged gears and arranged to be opened and closed by the operation of a cylinder. The grasping mechanism is pivotally supported so as to be movable back and forth on the track of the movement of the probe holding rod. Finally, a probe cutting mechanism is provided with a pair of probe grasping pawls which can be opened and closed by a cylinder, and a motor-driven cutter is supported for pivotal movement by the operation of a cylinder, the cutting mechanism being pivotally supported so as to be movable back and forth on the track of movement of the probe holding rod.

13 Claims, 14 Drawing Figures

AUTOMATIC PROBE FEEDING, SETTING AND WITHDRAWING APPARATUS

FIELD OF THE INVENTION

This invention relates generally to an apparatus for automatically feeding, setting in position and withdrawing a probe which is used for the sampling of molten steel, the measurement of temperature, and other testing practices in a furnace such as converter, an electric furnace, etc. More particularly, it relates to improvements in such automatic probe feeding, setting and withdrawing apparatus comprising a probe container case, a probe setting mechanism and a probe withdrawing and recovering mechanism.

DESCRIPTION OF PRIOR ART

Generally, the conventional automatic probe feeding, fixing and withdrawing apparatus of this type are constituted by a probe container case of a structure capable of containing the probes grouped according the type and the automatic removal of such probes, means for transferring each probe removed from the case, probe setting means designed to receive each probe transferred from the transfer means and functioning to permit such probe to stand uprightly and to swing just below the probe holding rod, and probe withdrawing and recovering means having a probe holding mechanism adapted for holding the probe lifted out of the furnace while attached to the probe holding rod and a cutting and recovering mechanism. All of these means and mechanisms are arranged to be operated on a remote control system.

However, both structural and operational problems persist for such conventional devices. For example, the probe dispensing mechanism of the probe container case is complicated structurally, unstable in operation and troublesome. In addition, the dispensing operation is attended by vehement vibration or impact, involving a high possibility of inflicting damage to the probes. Further, as the probe fitting and removing operations are performed by a same mechanism, the apparatus is subject to excessive damage due to high temperature gas or dust blown up from inside the furnace, resulting in frequent trouble or failure in operation. Moreover, the probe fixing mechanism in conventional apparatus has no means for countervailing the erroneous fixing of a wrong probe, so that in the event of such false operation, troublesome replacing work is necessitated, resulting in delayed probe fitting and removing work and a hindrance to the furnace operation.

Various measures have been proposed to overcome such problems, but there is available as yet no device which is free of such difficulties and can operate with its full capacity in a limited space and under bad environmental conditions, and the solution to these problems has been posed as the subject for study by the industry.

SUMMARY OF THE INVENTION

The primary object of the present invention is to provide an automatic probe feeding, setting and withdrawing apparatus which functions in an improved manner to ensure a stabilized operation and an improved operating efficiency to effectively solve the above-mentioned problems.

Another object of the present invention is to provide a probe container case equipped with a probe dispensing mechanism which allows an easy, smooth and stable probe dispensing operation.

A further object of the present invention is to provide a probe fitting mechanism which has an improved probe fitting function and is capable of eliminating the above-mentioned problems.

A still further object of the present invention is to provide an improved probe withdrawing and recovering means designed such that the withdrawal and recovery of the probe lifted up from inside the furnace can be accomplished by a separate device so as to prevent damage to the various means and elements attached to the block adapted to have the probe erected and turned immediately below the probe holding rod.

DESCRIPTION OF THE PREFERRED EMBODIMENT

Figure 1A:
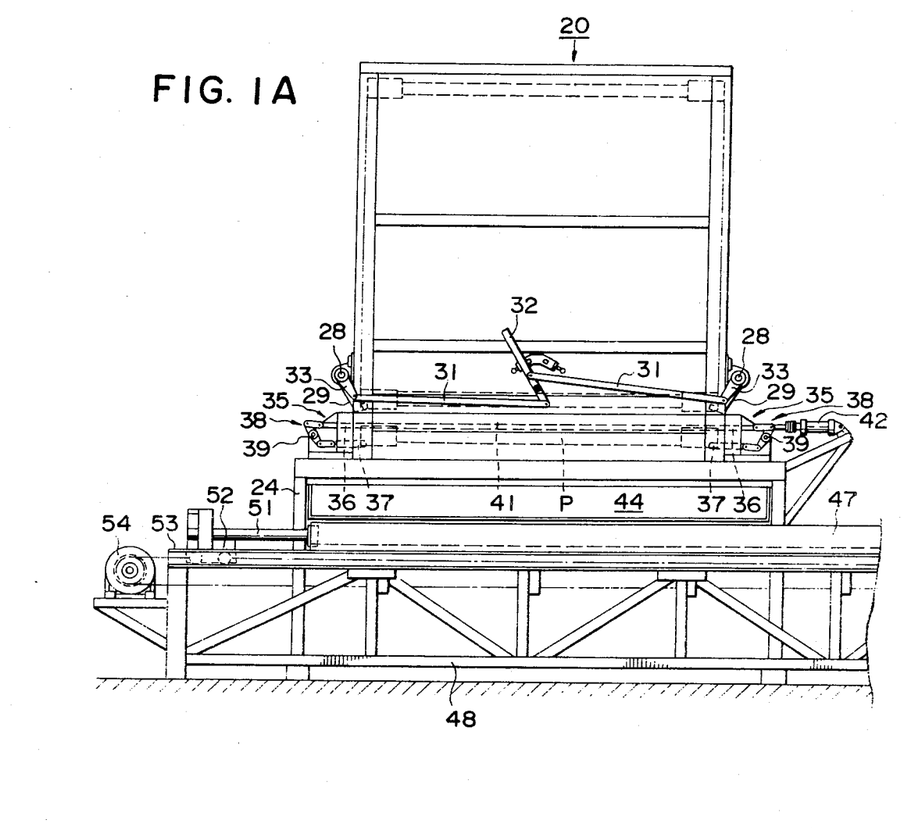
FIGS. 1A and 1B together form a general schematic side elevational view of the apparatus according to an embodiment of the present invention.
Figure 1B:
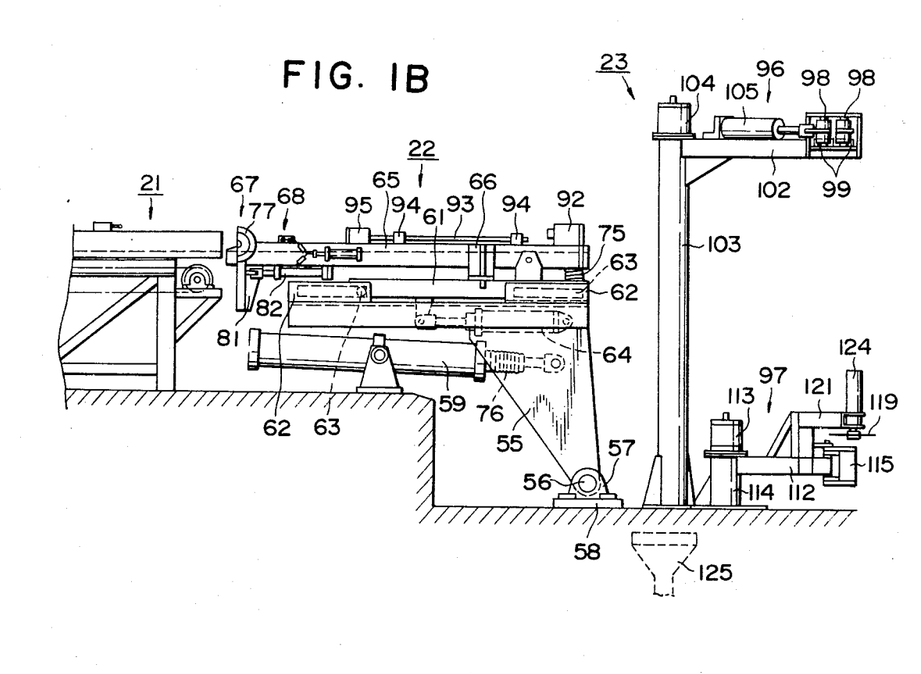
Figures 2A, 2B:
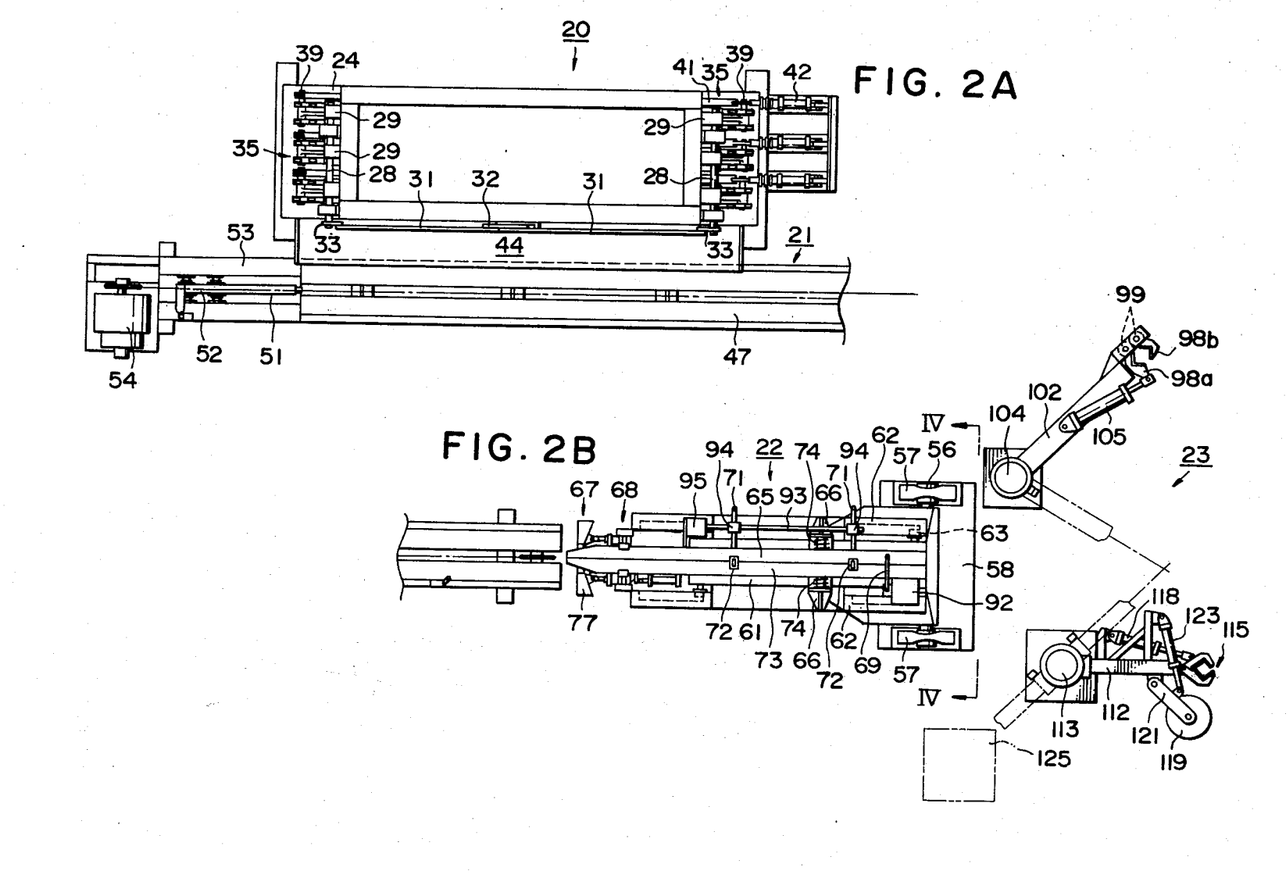
FIGS. 2A and 2B together form a top plan view of the apparatus shown in FIGS. 1A and 1B.

Referring to FIGS. 1 and 2, the apparatus according to the present invention is shown as comprising a probe container case 20, a mechanism 21 for carrying or transferring the probes dispensed from the container case, a probe setting mechanism 22 functioning to receive each probe transferred from the transfer mechanism and to effect an upright stance for each on the track of movement of a probe holding rod, and a probe withdrawal and recovery mechanism 23 designed to grasp the probe lifted out of the furnace and cut and recover it.

Figure 3:
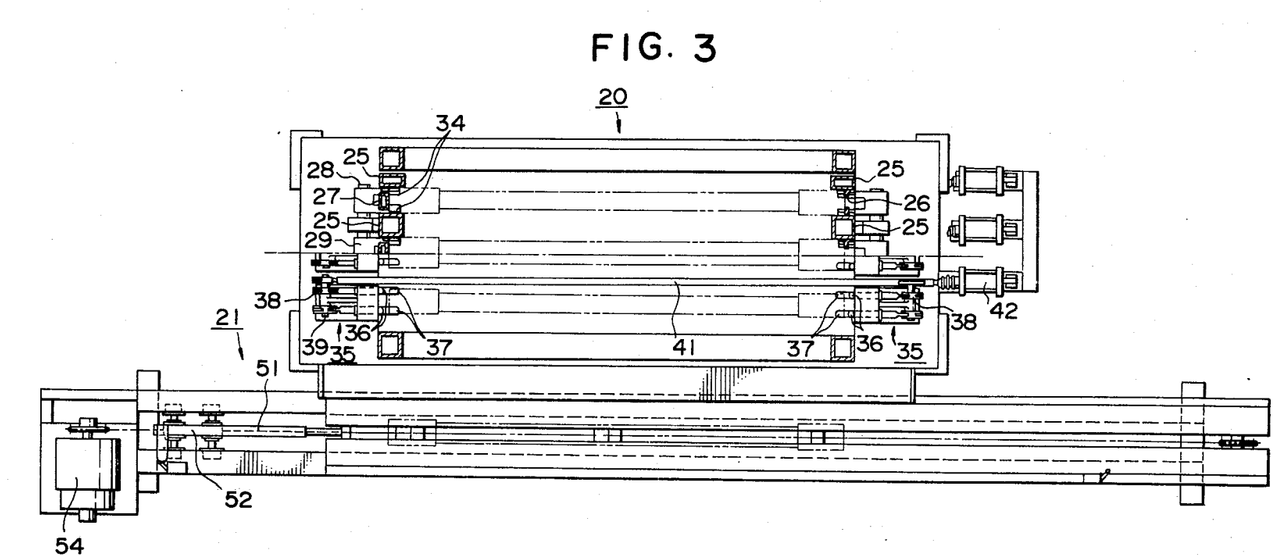
FIG. 3 is a part sectional and plan view of the probe container case portion of the apparatus taken along the line III—III of FIG. 5.
Figure 4:
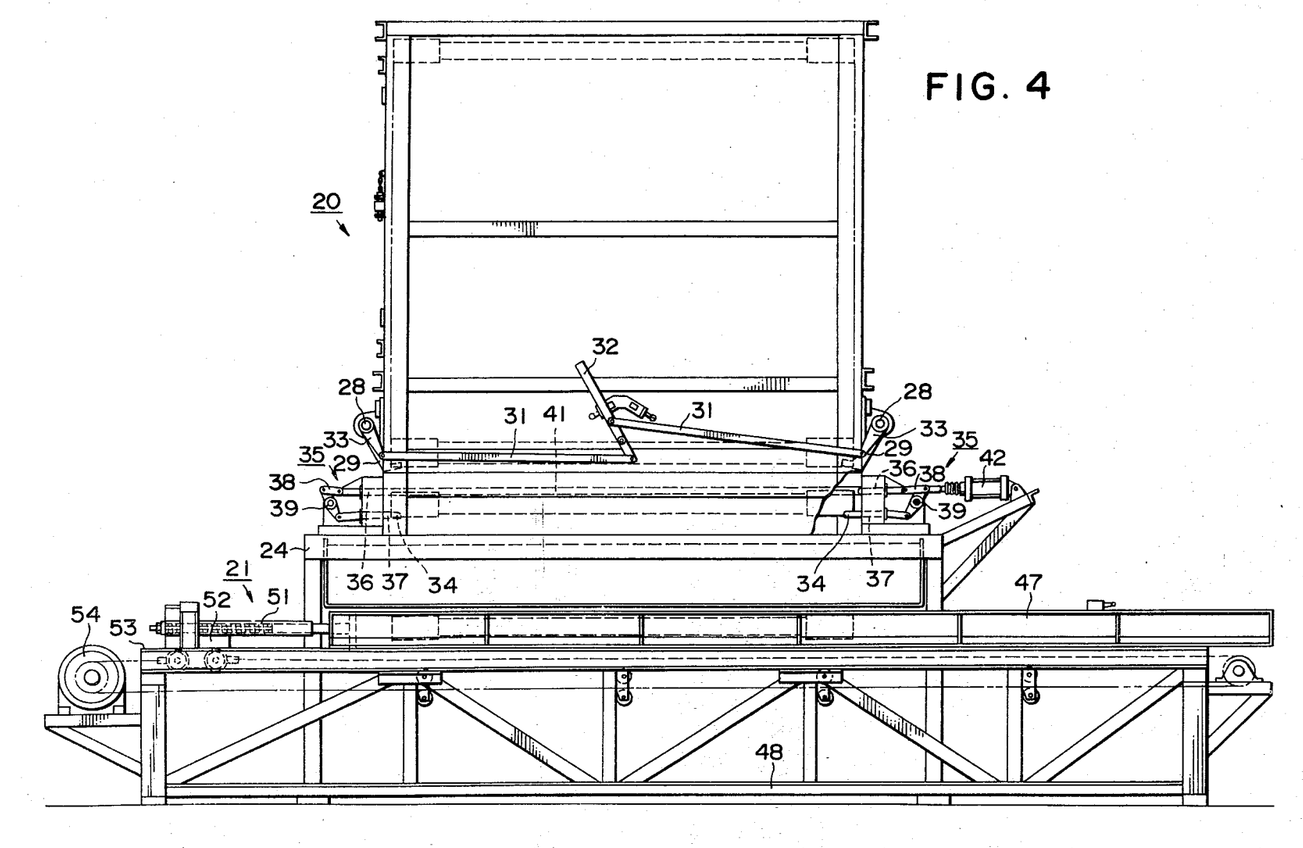
FIG. 4 is a front elevational view of the probe container case portion of FIG. 3.
Figure 5:
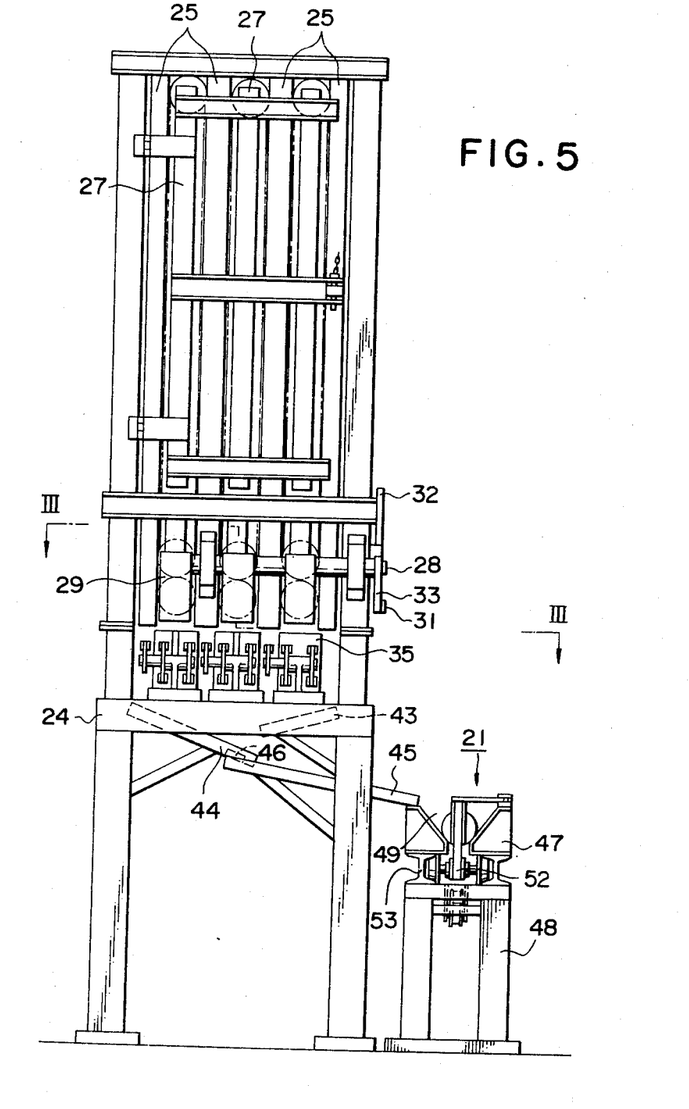
FIG. 5 is a side elevational view of the probe container case portion of FIG. 3.

The probe container case 20 is fixedly mounted on an underframe 24 and its side structure is formed by spacer pillars 25 (FIGS. 3 and 5) vertically disposed at suitable intervals. Guide plates 26 are provided on the front and a side of the probe and doors 27 designed to close the spaces between pillars 26 are mounted on the opposite side. Support shafts 28, 28 are disposed along both side walls of the bottom portion of the container case, and probe receiving pawls 29 adapted to support both ends of the probe are pivotally secured to the respective shafts opposite one another between the respective spacer pillars. There are also provided working bars 31 arranged to move in opposite directions in accordance with the turning of an operating lever 32 provided on the outer wall of the container case. Each working bar 31 is connected to the corresponding one of support shafts 28 by a connecting plate 33 so that both probe receiving pawls 29 will turn inwardly or outwardly simultaneously by the operation of lever 32 so as to hold or release the probe. Each of the probe receiving pawls is L-shaped so that its arm portions 34, 34 (FIG. 4) projecting from both ends thereof will insert between the upper and lower probes to receive the upper probe. Below each probe receiving pawl is provided a link-type supporting arm assembly 35 designed such that one probe is supported by each row of arms. Each row of this supporting arm assembly comprises four sections of upper and lower arms arranged in pairs of two. The upper and lower arms 36, 37 are secured to a three-piece link mechanism 38 arranged to operate in accordance with a turning motion of a support shaft 39 mounted horizontally on underframe 24 and parallel to supporting shaft 28 of the receiving pawl. Thus, the supporting arms on both sides are arranged such that every two arms on the upper and lower sides will move alternately back and forth and independently of the other row by means of a connecting bar 41 which is operated by a horizontal pneumatic cylinder 42 mounted on underframe 24. Numerals 43, 44 and 45 (FIG. 5) designate probe guides each of which is provided on its upper surface with an elastomeric coating for attenuating vibration or impact generated when the probe drops. 46 is a switch for confirming the proper fall of the probe.

The probe transfer means 21 for transferring the probes taken out of the probe container case to the probe fitting mechanism 22 comprises a support block 47 (FIG. 5) mounted on an underframe 48 and being provided on its surface with a V-shaped channel extending longitudinally so as to form a space 49. A probe push rod 51 (FIG. 2A), disposed for movement into space 49, is secured to a truck 52 slidably disposed on rails 53 supported on underframe 48, truck 52 being chain-driven by a motor 54 mounted on the rear portion of underframe 48. Thus, the rear end of the probe placed on block 47 is pushed by push rod 51 and is carried to the succeeding probe fitting mechanism 22.

The following is a description of probe fitting mechanism 22 according to this invention which functions to receive every probe carried there by transfer means 21 and to turn and erect it immediately below a probe holding rod so as to fit it in the probe holding rod. As shown in FIGS. 1B and 2B, this probe fitting mechanism 22 has a block 55 pivotally secured by a pivot pin 56 to bearings 57, 57 provided on a support 58, block 55 also being supported by a pneumatic cylinder 59 which operates to pivotally move the block. Mounted on the block is a movable plate 61 which is mounted on wheels 63 for sidewise movement on guide rails 62 by means of an operating pneumatic cylinder 64, rails 62 being disposed longitudinally along portions of the front and rear ends of the upper surface of the block. A probe fitting block 65 having a suitable length is fixed, while allowing a predetermined run-out, on brackets 66, 66 provided on movable plate 61. Probe fitting block 65 has at its front end a probe fitting guide assembly 67 and has a probe holding means 68 at its front portion adapted to hold the probe sidewise, as will be more clearly seen hereinafter. Block 65 also has a clamp bar 69 at its rear portion which is adapted to clamp the probe from above relative thereto. Also provided on a side wall of probe fitting block 65 are kick-up bars 71, 71 which extend through openings 72, 72 located in a V-shaped probe resting surface 73. Block 65 is cushioned laterally by buffer springs 74, 74 which support brackets 66, and the block is likewise cushioned vertically at its rearward end by a buffer spring 75 so as to thereby absorb both lateral and vertical run-out. In addition, a buffer spring 76 is provided for cylinder 59.

Probe fitting guide 67 comprises L-shaped split members 77, 77 having trumpet-shaped half-circular guide portions 78 (see FIG. 6), with its base portion being pivotally supported by a pivot pin 79 on a support block 81 provided at the underside of probe fitting block 65. These split members 77, 77 are connected to the ends of the flexible rods of two guide pneumatically operating cylinders 82, 82 mounted on fitting block 65 so as to operate simultaneously. When fitting the probe, both cylinders 82, 82 operate simultaneously to effect movement of guide portions 78 to their positions shown in phantom outline in FIG. 6, and upon completion of the fitting operation, guide portions 78 are restored to their original open position shown in solid outline in this FIGURE. It will be apparent that when guide assembly 67 is in its closed position, the centerline of the trumpet-shaped guide portions is aligned with the axis of the probe fixed on the fitting block.

Figure 6:
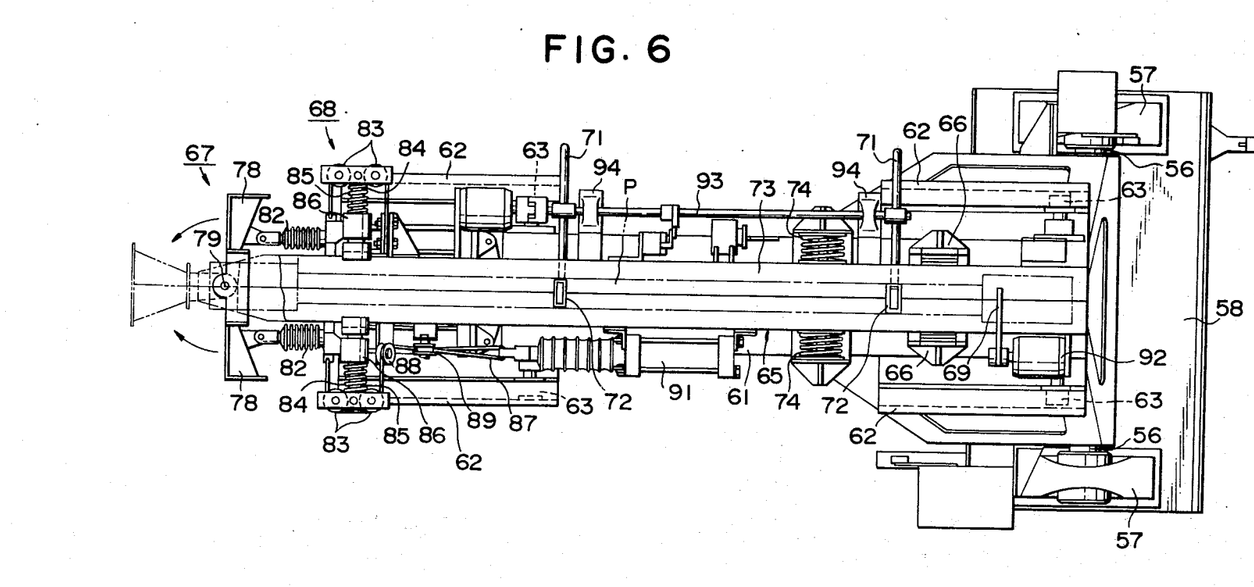
FIG. 6 is a plan view of the probe fitting mechanism of the invention.
Figure 7:
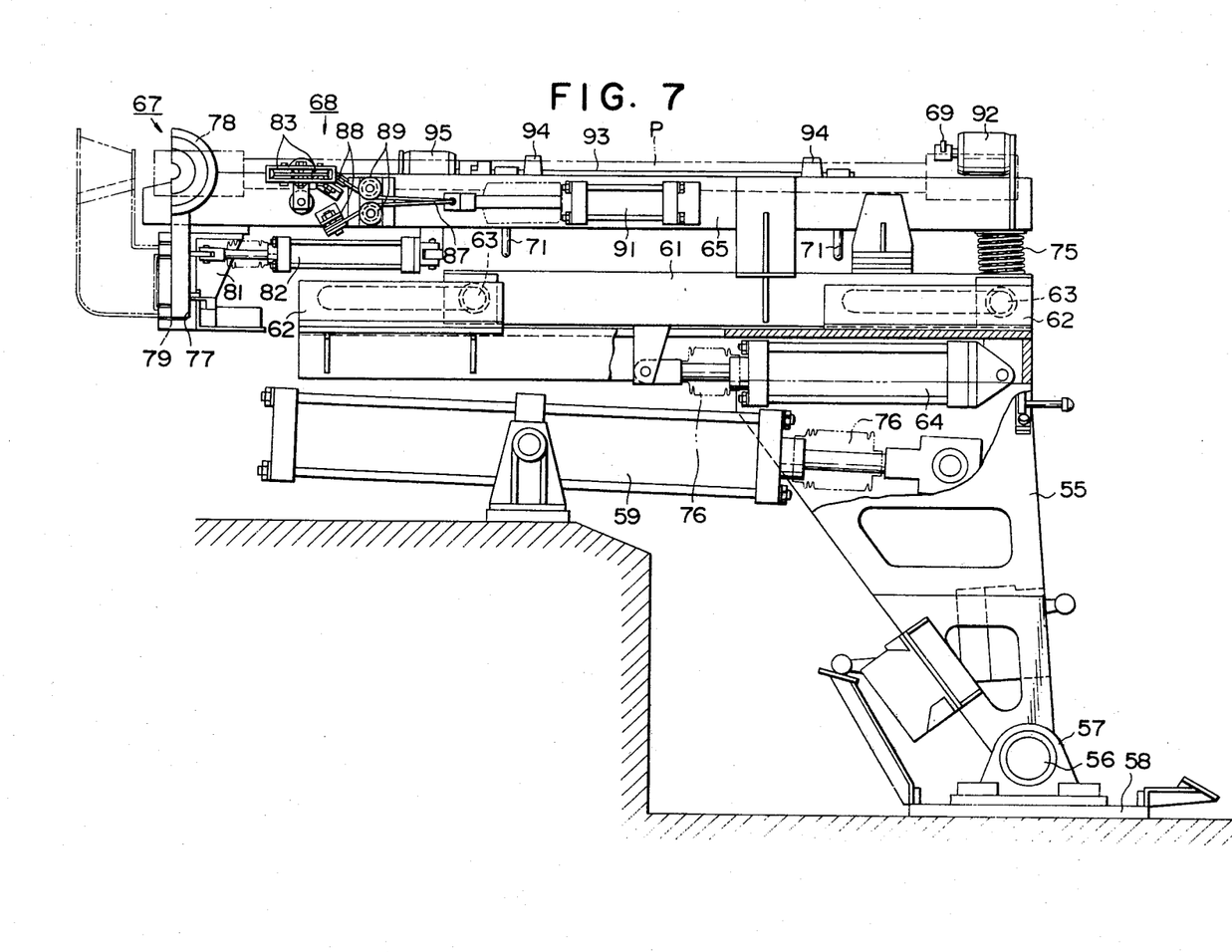
FIG. 7 is a front elevational view of the mechanism of FIG. 6.
Figure 8:
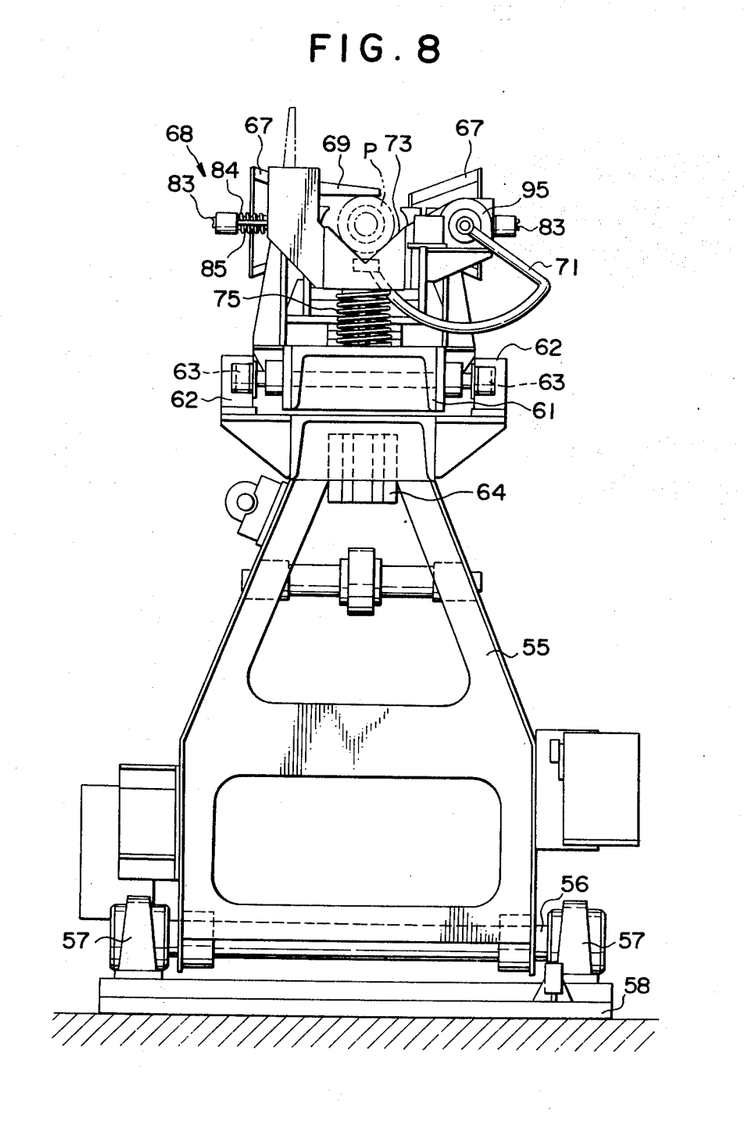
FIG. 8 is a side elevational view thereof.

Probe holding means 68 shown in FIGS. 6, 7 and 8, designed to hold and sidewise affix the probe placed on fitting block 65, includes a pair of horizontally disposed pulleys 83, 83 secured through springs 84 to the rear ends of respective clamp shafts 85, 85 slidably disposed in guides 86, 86 located in opposing relation on the probe fitting block. A taut rope 87 passes about pulleys 83, 83 as well as about a pair of pulleys 88, 88 angularly mounted on one side of the fitting block, and further about another pair of pulleys 89, 89 mounted on the side opposite pulleys 88, 88. In addition, the rope passes through the end of a rod of a clamping cylinder 91 mounted on block 65, with both ends of the rope being joined to the respective clamp shaft guide portions so that when the cylinder 91 operates rearwardly, both clamp shafts 85, 85 move forwardly, and when the cylinder operates forwardly, the clamp shafts are moved back by the action of springs 84, 84 mounted on the respective clamp shafts. The holding mechanism shown in the drawings is intended to be merely an illustrative example, so that the principle of the present invention is not to be limited to such a particular mechanism. For example, such a relatively complex pulley system is designed for a limited installation space for the apparatus, particularly in the width.

Clamp bar 69, adapted to fix the front end of the probe from the upper surface thereof, is operated by a pneumatic cylinder 92 mounted on probe fitting block 65. Probe kick-up bars 71, 71, which function to remove the wrong probe from the probe fitting block, are secured to both ends of a shaft 93 which is rotatably supported at both its ends by bearings 94, 94 located on a side of probe fitting block 65, with the foremost ends of the bars extending upwardly through openings 72, 72 located in the probe resting face of the fitting block so that they confront such face. In addition, shaft 93 is connected to the drive shaft of a motor 95 mounted on the probe fitting block so as to swing kick-up bars 71, 71 upwardly during operation of the motor.

The respective operating members in the probe fitting unit, such as clamp shafts 85, 85, movable plate 61, etc., in the probe holding mechanism, may be driven by a motor system employing a rack and pinion mechanism, instead of the cylinder system described above. Also, control of the series of operations of the apparatus is effected automatically on a remote control system by operating the limit switches provided at the appropriate positions.

The following is a description of probe withdrawal and recovery mechanism 23 which is designed to grasp the probe lifted up from inside of the furnace and to cut and recover it.

Figure 9:
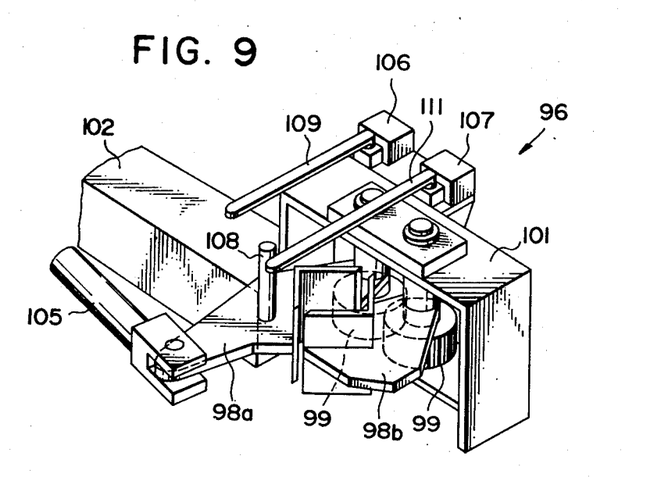
FIG. 9 is a perspective view of the probe holding means of the invention.
Figure 12:
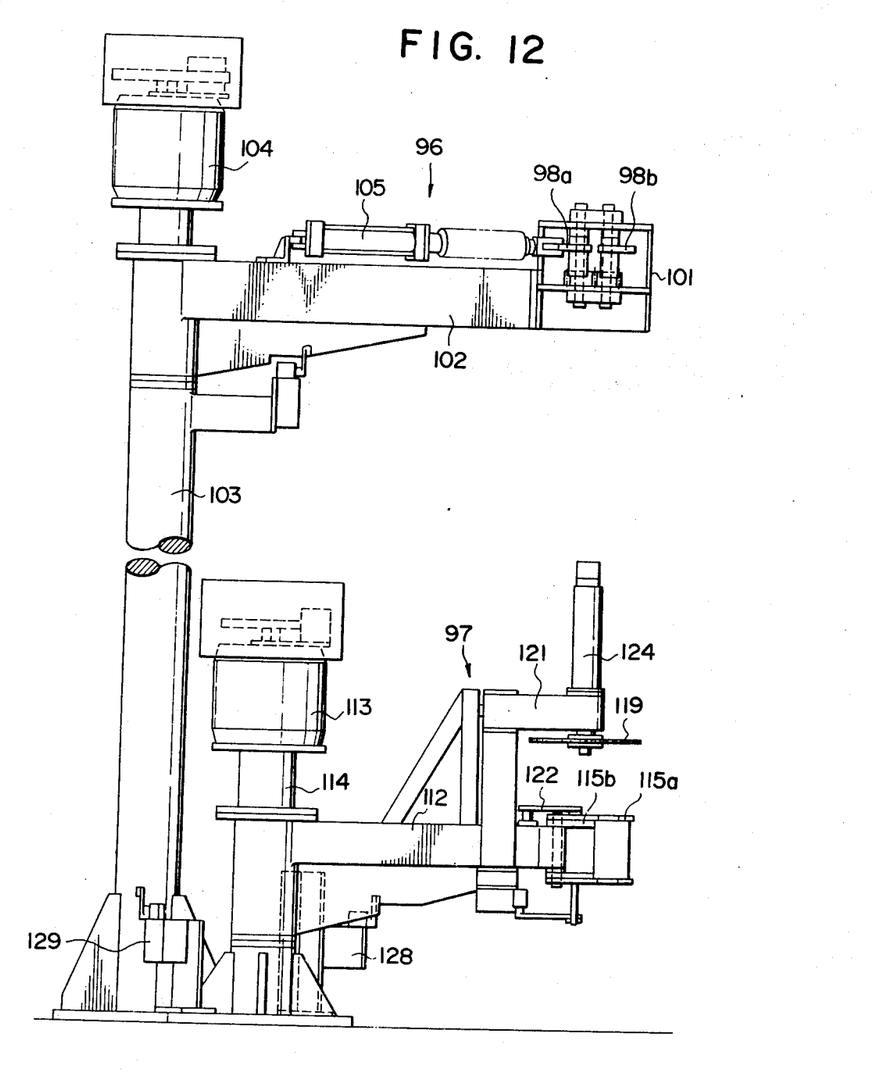
FIG. 12 is a front elevational view of the mechanism shown in FIG. 11.

The probe withdrawal and recovery mechanism of this invention, shown in FIGS. 1B and 2B, comprises a mechanism 96 for holding the upper portion of the probe lifted out of the furnace, and a mechanism 97 for grasping and cutting the lower portion of the probe and recovering it. This holding mechanism 96, also shown on an enlarged scale in FIG. 9, has a pair of grab pawls 98a, 98b pivotally secured to two meshed gears 99, 99 housed in a gear box 101, mounted at the end of an arm bar 102 supported by an upright standard 103 (FIG. 12) and being movable horizontally by a motor 104. The pawls are also connected to a pneumatic cylinder 105 secured to arm bar 102 so that pawls 98a, 98b may be opened and closed. Cylinder 105 is controlled by limit switches 106, 107 attached to gear box 101 and are operated by a pin 108 mounted on one of the grap pawls and two levers 109, 111 disposed on the track of movement of the pin, to thereby effect a controlled opening and closing movement of pawls 98a, 98b.

Figure 10:
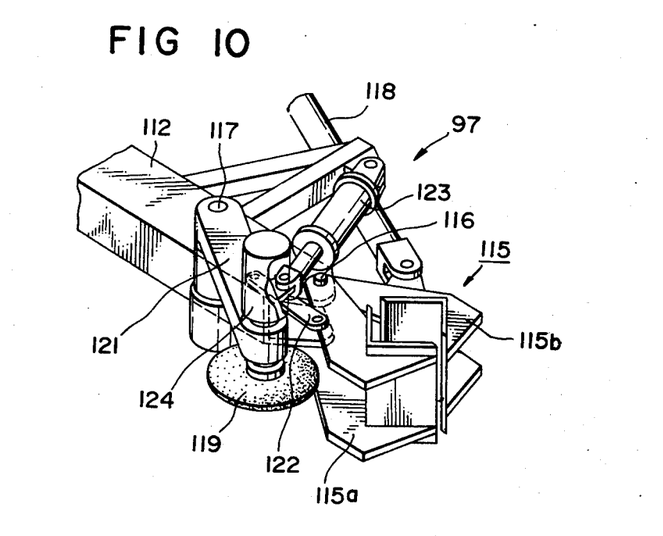
FIG. 10 is a perspective view of the probe cutting and recovering unit of the invention.
Figure 11:
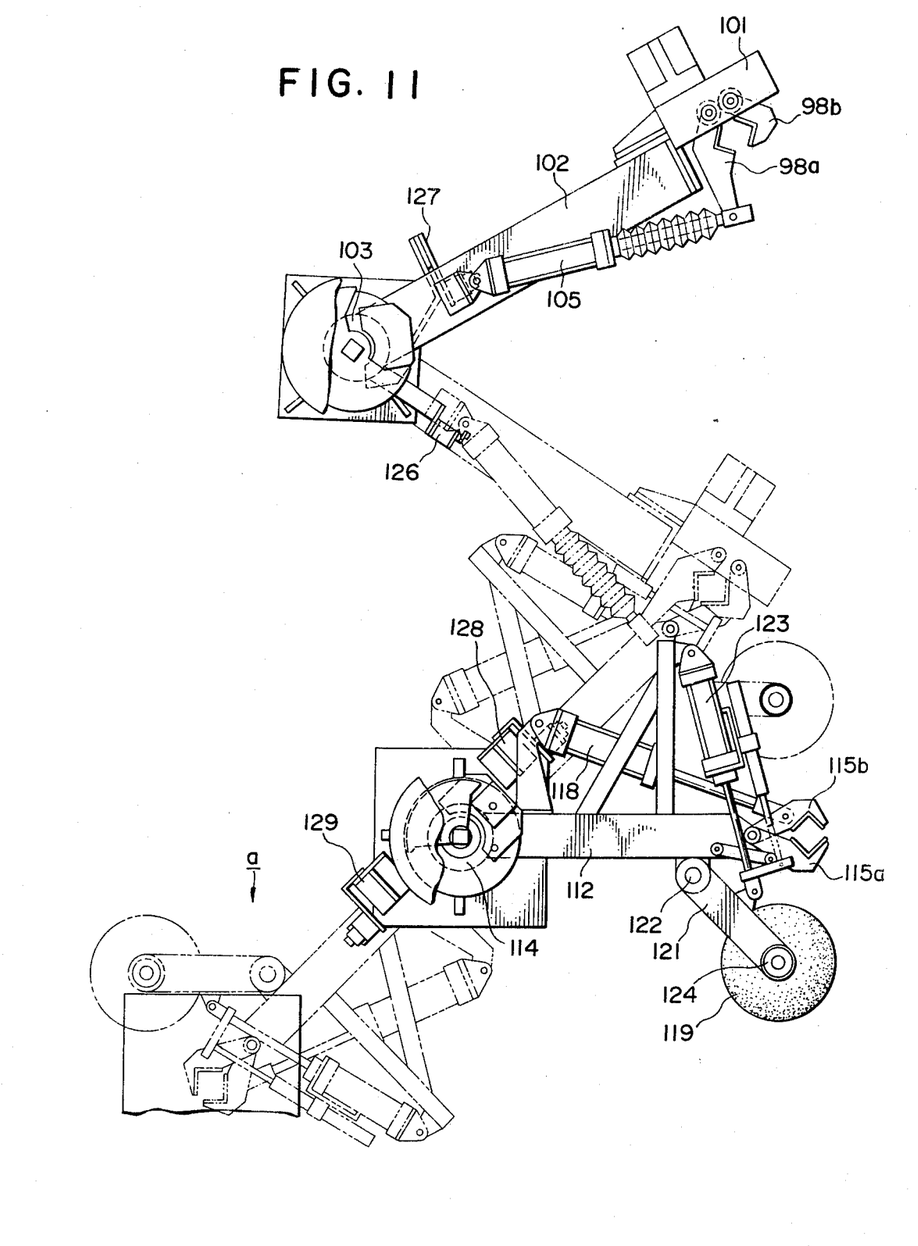
FIG. 11 is an enlarged plan view of the probe withdrawing and recovering mechanism of the invention.

Mechanism 97, designed for grasping and cutting the lower portion of the probe and recovering it, as shown in detail in FIGS. 10 and 11, includes an arm bar 112 arranged to be turned by a motor 113 (FIG. 12) and supported by an upright 114 disposed adjacent standard 103 of holding mechanism 96. Mechanism 97 further includes assembly 115 comprising a fixed pawl 115a pivotally mounted on a pivot 116 and mounted by a bar 117, and a movable pawl 115b connected to a pneumatic cylinder 118 secured to the bar 112 so that movable pawl 115b may be opened and closed by cylinder 118. Also provided at this section is a cutter disc 119 secured to a movable bar 121 pivotable about a pivot pin 122 above grab pawl 115 by a cylinder 123 secured to arm bar 112, cutter 119 being driven by a motor 124.

125 is a container for recovering the cut-out lower portion of the probe, this container being positioned above the track of of movement of grab pawl assembly 115 (FIG. 11). 126 and 127 are limit switches for stopping motor 104 which drives probe holding unit 96, limit switch 126 being operated at the probe grasping position and limit switch 127 being operated at the recessed position. 128 and 129 are limit switches for stopping motor 113 which drives recovery mechanism 97, switch 128 being operated at the grasping position and switch 129 being operated just above the recovery box.

Operation of the apparatus according to the present invention is as follows.

In the situation just before the probe is taken out, probe supporting arm assembly 35 is so arranged that upper arms 36 project out forwardly while lower arms 37 remain in a retracted position. Now, when the operation lever 32 is turned down to the right side when viewing FIG. 4, probe receiving pawsl 29, 29 supporting both ends of the probe assembly are simultaneously turned outwardly about their respective shafts 28, and upon being freed from pawls, 29, the entire probes of the particular row drop down to upper supporting arms 36 positioned therebelow. So, if, under this condition, operating lever 32 is again turned down to the left side as in FIG. 4, left and right arm portions 34, 34 of the respective probe receiving pawls 29, 29 are inserted in the space between the first and second probes from the bottom of probe assembly. However, no attempt is normally made to stop the fall of the probes from the probe container case by operation of lever 32, since receiving pawls 29 are maintained in their retracted position so that the probes in the container case will drop directly onto the associated supporting arms 36. This operation, that is, receiving and checking the probes by receiving pawls 29 by operating lever 32, is performed when making repairs or other works by separating container case 20 alone from interlocked mechanisms (35, 39, 38, 42) or when containing the probes in container case 20.

Then, cylinders 42 are operated rearwardly to allow upper supporting arms 36 to retract while allowing lower supporting arm 37 to project out forwardly, whereby the first probe alone drops down and is supported by the forwardly projecting lower supporting arms 37. When cylinders 42 are then operated reversely under this condition, lower supporting arms 37 are retracted so that the probe supported thereby falls down, while upper supporting arms 36 move forwardly to return to the original position to stay ready for receiving the next probe. On the other hand, the probe which has dropped rolls down on guides 43, 44, 45 to ride on probe transfer device 21. This completes the dispensing operation of the first probe.

It is possible to take out the probes one by one by repeating the aforedescribed operation. As the probe receiving pawls of each row are designed to operate simultaneously with each other, they are normally retained in their retracted position, and hence the probes of the other rows are supported by the probe supporting arms of the respective rows. Therefore, when in operation, receiving pawls 29 of each row remain separate from the probe assembly and hence the entire load is applied to the upper supporting arms, but this poses no serious problem as the receiving pawls are returned to the original supporting position immediately after the fall of the entire probes.

The probe P which has dropped from the probe container case rolls down on guides 43, 44, 45 to ride on support block 47 of probe transfer device 21, and as its rearward end is pushed by probe push rod 51 provided on truck 52 which is chain-driven by motor 54, this probe moves in the V-shaped channel to enter the next probe fitting mechanism 22.

When probe P which is carried by probe transfer device 21 moves to and rests upon V-channelled resting surface 73 of horizontally disposed probe fitting block 65, clamp cylinder 91 is operated to clamp the rear portion of the probe by clamp shafts 85, 85 while holding and fixing the fore portion of the probe by clamp bar 69. Thereafter, cylinder 59 is operated to turn up block 55 (to the right side in FIG. 7) about pivot 56 to the position above the track of movement of a probe holder rod (not shown), whereat the limit switch (not shown) is pushed at its fixed position to stop the fluid supply to cylinder 59 to allow block 55 to remain stationary at this position. Then guide operating cylinders 82, 82 are operated to turn split members 78, 78 forwardly to constitute a trumpet-shaped guide assembly (shown in phantom outline in FIG. 6). While maintaining this condition, a probe holding rod is lowered down to a position close to fitting guide assembly 67 and is retained at this position. In this case, the axial center of the guide assembly could be biased, but as the guide assembly is trumpet-shaped in consideration of such possibility, the axial centers of both the probe and the probe holding rod can be automatically aligned. When the probe is positioned immediately below the probe holding rod, fitting guide assembly 67 is returned to the original position and cylinder 64 is operated to raise up fitting block 65, whereby guide assembly 67 is mounted on the probe holding rod and the probe is fitted on the probe holding rod with the additional rising movement. When the probe has been thus perfectly fitted in position, clamp cylinders 91, 92 are operated to release the probe, and upon completion of these operations, cylinder 59 is operated to permit plate or block 55 to return to the original horizontal position.

The above-described process can set one piece of probe in position. In the above process, should a wrong probe be erroneously carried to fitting block 65, motor 95 is operated to allow kick-up bars 71, 71 to swing upwardly about shaft 93 to thereby remove such wrong probe from fitting block 65.

The probe which has been properly fitted to the probe holding rod is then inserted into the furnace, and upon completion of the desired measurement for a set period of time, the probe holding rod rises up and the cutting and recovery of the probe is accomplished by probe withdrawal mechanism 23. During this time, probe fitting mechanism 22 receives no effect of heat since it has already returned to and remains at its original position. However, according to the conventional devices, since the entire fitting mechanism is maintained at the position of the fitting operation and the probe is removed by holding it with clampers attached to such mechanism, the entire mechanism is exposed to heat radiation or high temperature discharge gas blown up from inside the furnace so as to suffer excessive damage.

When the probe is lifted up out of the furnace, arm bars 102, 112 of holding mechanism 96 and cutting and recovering mechanism 97, respectively, are turned about their respective support poles 102, 114 to their predetermined positions, whereat the respective grab pawl driving cylinders 105, 118 are operated to hold the upper portion of the probe with pawls 98a, 98b and the lower portion with pawls 115a, 115b, and as cutting cylinder 123 is then operated, movable bar 121 is turned to let rotating cutter 119 touch the probe to cut it gradually. As the probe is cut, cutter 119 is returned to its original position and then arm bar 112 is moved back to the position of recovery box 125 (position a shown in phantom outline in FIG. 11) to open grab pawl 115, whereby the cut-out lower portion of the probe drops into recovery container 125. Thereafter, arm bar 112 is returned to its original standby position. On the other hand, the remaining upper portion of the probe is dropped into the furnace by spreading out grab pawls 115a, 115b after cutting and recovering mechanism 97 has recessed to its normal position, and then arm 102 is returned to its original standby position. The operations of the cylinders and motors of the respective mechanisms are remote-controlled as in any normal manner by a control panel setting.

As described above, the device of this invention is capable of automatically and positively accomplishing the entire process from dispensing and feeding of the probes to setting and withdrawal thereof all with stabilized performance, so that it provides a marvelous effect in the sampling of molten steel, the measurement of temperature and other testing practices. This is effected by the structure, function and effect of the respective principle mechanisms constituting the present invention. More specifically, the probe container case according to this invention is provided with a probe dispensing mechanism comprising probe receiving pawls actuated by a lever operation and a fourpiece probe supporting arm assembly arranged such that the upper and lower paired arms will alternately move back and forth through a link mechanism operated by a cylinder or other drive means, and such probe dispensing mechansim itself is designed to be operated with a turning motion of the support shafts and link connection, so that the mechanism is quite simple, high in strength, trouble-free and capable of an always stable operation. If a probe selection switch is provided, it is possible to optionally select any desired probe by the indication of such switch. Also, as the probe dispensation is performed in a step-by-step manner, no vibration or impact is produced during such dispensing operation, thus allowing minimization of the possibility of causing damage to the probes.

The probe fitting mechanism features the provision of a movable block slidable through a given stroke on a support arranged to be swivelled by a cylinder, probe clamping means and probe fitting guides attached to such movable block, and a probe fitting block provided with a probe kick-up means for removing the erroneously supplied probe. This mechanism is entirely made of a buffer structure so as to minimize vibration or impact produced when carrying and fitting the probe, and in consideration of the installation space, the operating systems, units, etc., of the respective mechanisms are constructed compactly. Further, all moving parts are high in strength and durability, and pivotal joints and sliding systems are employed to well withstand repeated operations.

Thus, the device of this invention is capable of a mechanically stabilized operation, and as it is capable of ridding an erroneously fed probe, the time required for disposing of such miscarriage is greatly lessened. Also, as each mechanism stays free of heat influence by heat radiation or high temperature discharge gas blown up from the inside of the furnace, it suffers no damage or failure due to such heat influence. Thus, an always stabilized probe fitting function can be maintained regardless of the kind and number of probes treated.

The probe withdrawal and recovery system comprises a clamping mechanism designed to hold the upper and lower portions of the probe and a cutting mechanism provided integral with the lower clamping mechanism, and an arrangement is also made such that each probe can be recovered on the track of movement of the lower clamping mechanism, so that the withdrawal and recovery of the probes can be accomplished with ease and quickly, and also use of a motor or cylinder for the drive of each mechanism always ensures a smooth and stabilized operation. Although the clamping and cutting of the probes are performed above the furnace, each mechanism returns, upon completion of the cutting operation, to the position where it remains free of any influence of heat in the furnace, so that each mechanism receives little influence of heat, thus allowing highly stabilized operation even under bad environmental conditions.

Obviously, many other modifications and variations of the present invention are made possible in the light of the above teachings. It is to be therefore understood that within the scope of the appended claims the invention may be practiced otherwise than as specifically described.

What is claimed is:

1. An automatic probe feeding, setting and withdrawing apparatus comprising, in combination: a probe container case provided with a probe dispensing mechanism comprising rows of probe supporting arms, each row of said arms being arranged in two vertically spaced stages and in pairs of two for reciprocation inwardly and outwardly from the both sides of a bottom portion of said case by a link mechanism; probe transfer means provided with a motor-driven probe push member at an end of a carriage board formed with a V-shaped channel in its surface; probe setting means comprising a movable block provided for sliding movement on a board pivotally supported in close proximity to one end of said probe transfer means, and a probe fitting block disposed parallel to said movable block and equipped at both ends thereof with probe clamps adapted for holding the probe from its sides and upper surface as well as having at its front end a pair of swingable probe fitting guides, said probe fitting block being also provided at a side thereof with bars designed to kick up the probe through openings formed in the probe resting surface thereof; and probe withdrawing and recovering means comprising a probe grasping mechanism having a pair of pawls arranged for opening and closing to grasp the upper portion of the probe, said mechanism being pivotally supported to be movable back and forth on the track of movement of a probe holding rod, and a probe cutting mechanism having a motor-driven cutter attached with a pair of swingably supported pawls arranged for opening and closing to grasp the lower portion of the probe, said mechanism being pivotally supported to be movable back and forth on the track of movement of a probe holding rod.

2. The apparatus as claimed in claim 1, wherein probe receiving pawls interlocked by a lever operation are provided immediately above the probe dispensing mechanism.

3. The apparatus as claimed in claim 1, wherein said probe container case has both its side portions formed of a plurality of spacer pillars arranged uprightly at predetermined intervals, and guide plates are provided between said spacer pillars in one side of the case and doors closing the spaces between said spacer pillars are provided in the other side.

4. The apparatus as claimed in claim 2, wherein said operating lever is pivotally joined to the outer wall of said container case, and a pair of working bars pivotally joined to said lever at opposite sides of the joined point of said lever with the outer wall of said case are pivotally joined through respective connecting bars to supporting shafts which are provided at both sides of said container case, with an L-shaped receiving pawl assembly being pivotally joined to each of said supporting shaft.

5. The apparatus as claimed in claim 1, wherein said probe push member comprises a truck slidable on rails laid on an underframe and a push rod secured to an end of said truck.

6. The apparatus as claimed in claim 1, wherein the probe clamps comprise a probe holding means for holding the probe from both sides thereof and a clamp bar for holding and fixing the probe from above thereof.

7. The apparatus as claimed in claim 6, wherein said probe holding means comprises guides provided opposite one another in the radial direction of the probe, and a clamp shaft slidably passed and supported in said guides.

8. The apparatus as claimed in claim 6, wherein said clamp bar is swingably secured to an associated cylinder.

9. The apparatus as claimed in claim 1, wherein one end of each of said probe kick-up bars is positioned in the corresponding one of said openings and its other end is fixed to a shaft pivotally supported parallel to the movable block, said one end of said bars being turned with the rotation of said shaft to push up the probe.

10. The apparatus as claimed in claim 1, wherein a buffer member is disposed between said movable block and said probe fitting block.

11. The apparatus as claimed in claim 1, wherein said pair of pawls adapted for grabbing the upper portion of the probe are pivotally joined to respective meshed gears mounted at an end of an arm bar swingably supported by a support pole.

12. The apparatus as claimed in claim 1, wherein said pair of pawls adapted for grasping the lower portion of the probe comprise a fixed pawl and a movable pawl pivotally supported by a single pivot positioned on an end bar swingably supported by a supporting pole, said movable pawl being arranged for opening and closing by the operation of a cylinder.

13. The apparatus as claimed in claim 12, wherein a motordriven cutter is attached to a movable bar pivotally secured to said end bar swingably supported by a supporting pole.

* * * * *